United States Patent
Hruska et al.

(10) Patent No.: US 7,172,580 B2
(45) Date of Patent: Feb. 6, 2007

(54) HEMOSTATIC VALVE ASSEMBLY

(75) Inventors: Christopher L. Hruska, Bloomington, IN (US); Christopher G. Dixon, Bloomington, IN (US); Aaron Barr, Fishers, IN (US); Ram H. Paul, Jr., Bloomington, IN (US); Alan A. Eller, Plainfield, IN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/009,587

(22) Filed: Dec. 10, 2004

(65) Prior Publication Data

US 2005/0171479 A1 Aug. 4, 2005

Related U.S. Application Data

(60) Provisional application No. 60/576,665, filed on Jun. 3, 2004, provisional application No. 60/529,179, filed on Dec. 11, 2003.

(51) Int. Cl.
*A61M 5/00* (2006.01)

(52) U.S. Cl. ............ 604/248; 604/167.05; 604/167.06; 251/149.1; 606/108

(58) Field of Classification Search ........ 604/236–237, 604/247–249, 288.03, 303, 171–172, 164.01–164.1, 604/167.01–167.6, 163.4, 32, 34, 99.02–99.4; 251/149.1, 149.9; 606/13, 108
See application file for complete search history.

(56) References Cited

U.S. PATENT DOCUMENTS

| | | | |
|---|---|---|---|
| 2,321,336 A | 6/1943 | Tondreau | |
| 2,416,391 A | 2/1947 | Hixson | |
| 2,844,351 A | 7/1958 | Smith | |
| 3,185,179 A | 5/1965 | Harautuneian | |
| 3,304,934 A | 2/1967 | Bautista | |
| 3,329,390 A | 7/1967 | Hulsey | |
| 3,599,637 A | 8/1971 | Schwartz | |
| 4,000,739 A | 1/1977 | Stevens | |
| 4,016,879 A | 4/1977 | Mellor | |
| 4,063,555 A | 12/1977 | Ulinder | |
| 4,239,184 A * | 12/1980 | Dudar | ............ 251/149.6 |
| 4,243,034 A | 1/1981 | Brandt | |
| 4,311,137 A | 1/1982 | Gerard | |

(Continued)

FOREIGN PATENT DOCUMENTS

EP 0 344 907 B1 12/1989

*Primary Examiner*—Nicholas D. Lucchesi
*Assistant Examiner*—Christopher Koharski
(74) *Attorney, Agent, or Firm*—Brinks Hofer Gilson Lione

(57) ABSTRACT

An iris-type valve assembly comprises a base, a rotatable member, and an elongated elastomeric valve sheath. The distal end of the valve sheath is secured to the base, and the proximal end of the valve sheath is secured to the rotatable member. At least one of the valve sheath ends includes a flange that is secured to a valve-receiving surface of the base or the rotatable member. The base and the rotatable member are aligned to define a passageway therethrough for passage of an interventional device. The valve sheath is disposed along the passageway and has a longitudinal opening therethrough for passage of the interventional device. Upon rotation of the rotatable member relative to the base, the longitudinal opening of the valve sheath is selectively constrictable to comprise a seal around the interventional device.

14 Claims, 14 Drawing Sheets

U.S. PATENT DOCUMENTS

| | | |
|---|---|---|
| 4,314,555 A | 2/1982 | Sagae |
| 4,424,833 A | 1/1984 | Spector et al. |
| 4,540,411 A | 9/1985 | Bodicky |
| 4,580,573 A | 4/1986 | Quinn |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,798,594 A | 1/1989 | Hillstead |
| 4,895,565 A | 1/1990 | Hillstead |
| 4,929,235 A | 5/1990 | Merry et al. |
| 4,932,633 A | 6/1990 | Johnson et al. |
| 4,978,341 A | 12/1990 | Niederhauser |
| 5,000,745 A | 3/1991 | Guest et al. |
| 5,006,113 A | 4/1991 | Fischer |
| 5,009,391 A | 4/1991 | Steigerwald |
| 5,053,013 A | 10/1991 | Ensminger et al. |
| 5,066,285 A | 11/1991 | Hillstead |
| 5,102,395 A | 4/1992 | Cheer et al. |
| 5,104,389 A * | 4/1992 | Deem et al. ................. 604/264 |
| 5,154,701 A | 10/1992 | Cheer et al. |
| 5,158,533 A * | 10/1992 | Strauss et al. ............. 604/6.09 |
| 5,158,553 A | 10/1992 | Berry et al. |
| 5,167,637 A | 12/1992 | Okada et al. |
| 5,176,652 A | 1/1993 | Littrell |
| 5,211,370 A | 5/1993 | Powers |
| 5,242,413 A | 9/1993 | Heiliger |
| 5,256,150 A | 10/1993 | Quiachon et al. |
| 5,267,966 A | 12/1993 | Paul |
| 5,304,156 A | 4/1994 | Sylvanowicz et al. |
| 5,350,363 A | 9/1994 | Goode et al. |
| 5,350,364 A * | 9/1994 | Stephens et al. ........ 604/167.06 |
| 5,376,077 A | 12/1994 | Gomringer |
| 5,395,349 A | 3/1995 | Quiachon et al. |
| 5,395,352 A | 3/1995 | Penny |
| 5,409,463 A | 4/1995 | Thomas et al. |
| 5,484,418 A | 1/1996 | Quiachon et al. |
| 5,538,505 A | 7/1996 | Weinstein et al. |
| 5,613,956 A | 3/1997 | Patterson et al. |
| 5,643,227 A | 7/1997 | Stevens |
| 5,653,697 A | 8/1997 | Quiachon et al. |
| 5,702,370 A | 12/1997 | Sylvanowicz et al. |
| 5,779,681 A | 7/1998 | Bonn |
| 5,895,376 A | 4/1999 | Schwartz et al. |
| 5,935,112 A * | 8/1999 | Stevens et al. ............. 604/256 |
| 5,935,122 A | 8/1999 | Fourkas et al. |
| 6,099,505 A * | 8/2000 | Ryan et al. ............ 604/167.04 |
| 6,197,016 B1 | 3/2001 | Fourkas et al. |
| 6,221,057 B1 | 4/2001 | Schwartz et al. |
| 6,416,499 B2 | 7/2002 | Paul, Jr. |
| 6,562,049 B1 | 5/2003 | Norlander et al. |
| 6,610,031 B1 * | 8/2003 | Chin .................... 604/167.04 |
| 2003/0144670 A1 | 7/2003 | Pavcnik et al. |
| 2003/0216771 A1 | 11/2003 | Osypka et al. |

* cited by examiner

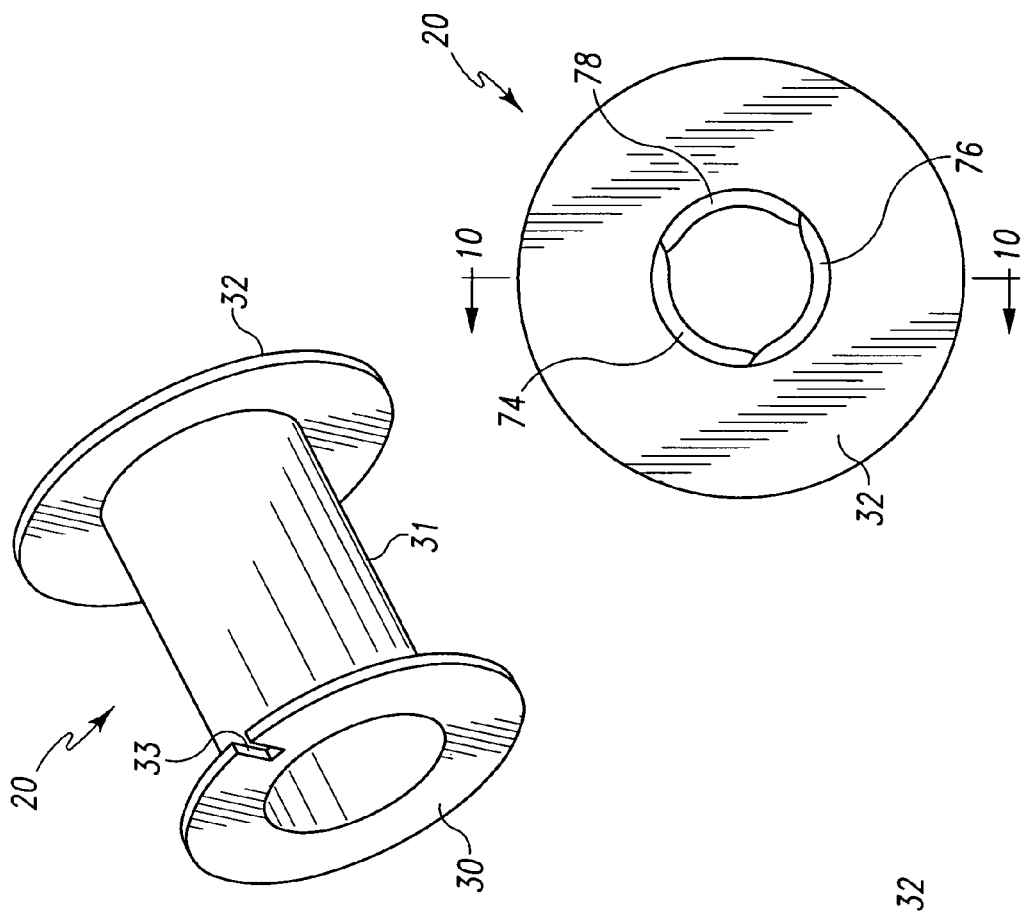
Fig. 9
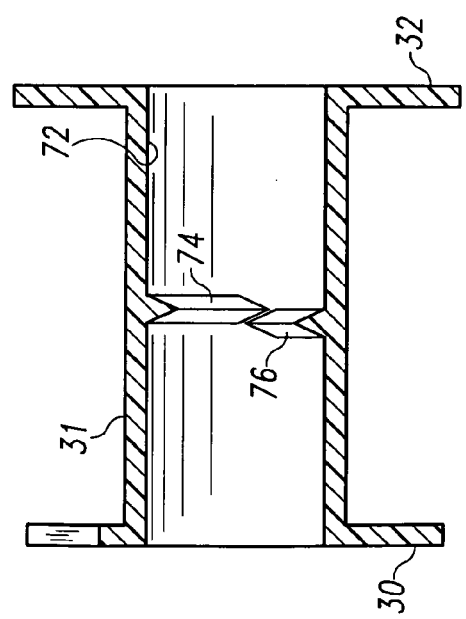
Fig. 11
Fig. 10

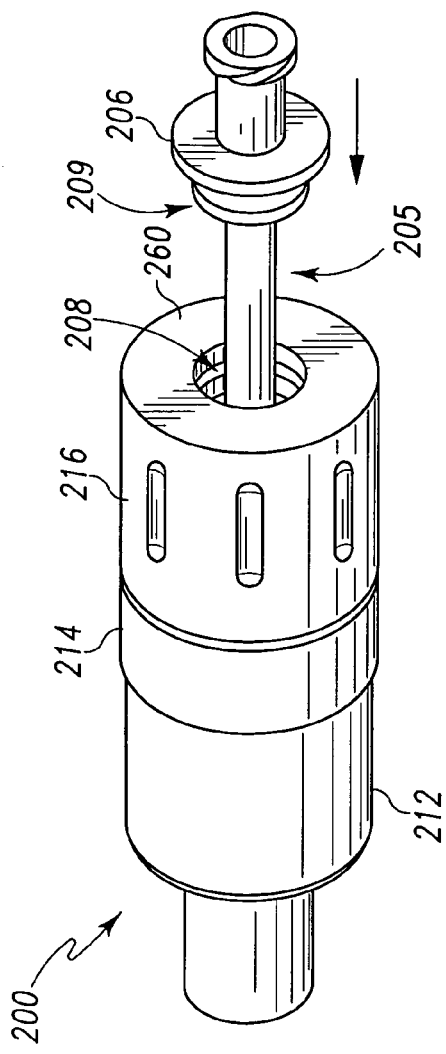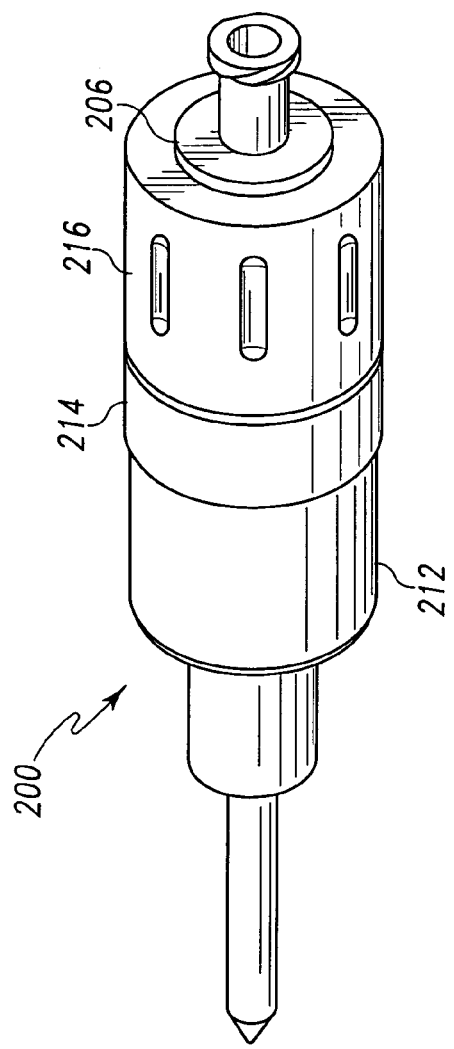
Fig. 19
Fig. 20

HEMOSTATIC VALVE ASSEMBLY

RELATED APPLICATIONS

The present patent document claims the benefit of the filing date under 35 U.S.C. §119(e) of Provisional U.S. Patent Application Ser. No. 60/529,179, filed Dec. 11, 2003, and Provisional U.S. Patent Application Ser. No. 60/576,665, filed Jun. 3, 2004, which are hereby incorporated by reference.

BACKGROUND

1. Technical Field

The present application relates generally to medical devices, and more particularly, to a hemostatic valve assembly for controlling the flow of fluids through a medical device.

2. Background Information

A variety of well-known medical procedures are performed by introducing an interventional device such as a catheter, trocar, sheath, stent and the like into a vessel in a patient's body. Typical procedures for introducing an interventional device into a blood vessel include the well-known Seldinger technique. The Seldinger technique involves opening a blood vessel with a needle, inserting a wire guide into the vessel through the lumen of the needle, withdrawing the needle and inserting a dilator over the wire guide. The dilator is located inside an introducer sheath which is also inserted into the vessel, and the dilator is sealed to the sheath by a hemostatic valve through which the dilator passes. The dilator is thereafter removed, and an interventional device is inserted through the sheath and hemostatic valve into the vessel.

During performance of the Seldinger technique and other interventional procedures, care must be taken to avoid the undesirable introduction or leakage of air into the vessel (air embolism), as well as the undesirable leakage of blood, other bodily fluids or cavity-pressurizing gas from the patient. As procedures for introducing catheters and other interventional devices have become more widely accepted, the procedures have become more diverse, and the variety of sizes and types of such devices employed has grown dramatically. As a result, the risk of inward or outward leakage of fluids has increased.

One known way to minimize such leakage is to provide one or more disk-like gaskets in an elongated passageway of a device through which fluids may pass into or out of the body. Such disks have opposing surfaces and often include one or more slits extending partially across each of said surfaces and extending inwardly toward the interior of the disk. A generally axial opening is provided between the slits to provide a sealable path for insertion of an interventional device through the disks. Such disks are described in, among others, U.S. Pat. Nos. 5,006,113 and 6,416,499, assigned to the assignee herein. The '113 and the '499 patents are incorporated by reference. Such devices are generally effective for sealing large diameter devices, but are often less effective for sealing smaller diameter devices, particularly after the earlier passage of a large diameter device.

Another type of valve that is presently in use for sealing elongated passages in a medical device to prevent passage of fluids is known as an iris valve. An iris valve is described in U.S. Pat. No. 5,158,553, incorporated by reference herein. The valve described in the '553 patent comprises a valve hub that is joined to a catheter-type device, and a rotatable cap that is joined to the hub. An elastomeric sleeve is positioned in an opening through the interior of the valve body. Each end of the elastomeric sleeve is joined to the rotatable cap by wrapping and clamping the respective end around a clamping mechanism. When the cap is rotated in a first direction, the circular opening of the elastomeric sleeve is fully opened. When the cap is rotated in a second direction opposite the first direction, the elastomeric sleeve is twisted intermediate the two ends to effect closure of the circular opening. Due to the elastomeric properties of the sleeve, the circular opening of the elastomeric sleeve constricts as the cap is rotated to effect closure.

Although the valve of the '553 patent is generally effective for sealing sheaths of certain sizes and compositions, the general design of the valve assembly of the '553 patent has certain shortcomings. For example, the manner of engaging the ends of the seal to the respective hub and cap is less than optimal. Such ends are capable of disengagement, which destroys the ability of the valve to form a seal. In addition, the seal does not include provisions to prevent recoil of the seal after rotation of the rotatable cap to position the seal in a desired position. As a result, if the operator relaxes the rotational pressure on the valve, the seal can revert, or recoil, to its original (unsealed) position. Yet another problem with the iris valve assembly as described in the '553 patent is that longitudinally extending gaps or channels are capable of being formed along the seal, which gaps or channels can extend through the valve after rotation of the valve to the closed position. When such gaps or channels are present, fluid can leak through them in the valve seal. Furthermore, the configuration of such valves renders them subject to tearing.

It would be desirable to provide a valve assembly that overcomes the problems associated with prior art iris valves, and that effectively combines the advantages of disk valves and iris valves. It would be desirable to provide an iris valve that provides an effective seal of the internal passageway of an introducer sheath or like medical device with a high degree of effectiveness when no interventional device lies across the seal or valve, and that is also capable of providing an acceptable seal when devices of varying diameters are introduced therein. It would also be desirable to provide an iris valve capable of inhibiting recoil following rotation of the valve member, and that has axial ends that are securely affixed in the valve. It would further be desirable to provide an iris valve that is capable of resisting the formation of gaps or channels, and is capable of resisting tearing when penetrated by an interventional device of large diameter. Finally, it would also be desirable to have a seal that tolerates repeated insertions and withdrawals of interventional devices without appreciable decrease in the performance characteristics of the seal or valve.

BRIEF SUMMARY

The present invention addresses the problems of the prior art.

In one version thereof, the present invention comprises a valve assembly for controlling a flow of fluid. The valve assembly comprises a base member, a rotatable member, and an elastomeric valve member. The base member, rotatable member and elastomeric valve member each have a proximal end and a distal end. The valve member distal end is secured to the base member and the valve member proximal end is secured to the rotatable member. At least one of the valve member ends comprises a flange secured to a valve-receiving surface of the respective base member or rotatable member. The base member proximal end and the rotatable member distal end are engaged in a manner to permit relative rotation therebetween. The base member and the rotatable member are aligned to define an elongated passageway therethrough for passage of an interventional device. The elastomeric valve member is disposed along the passageway and has a longitudinal opening therethrough for passage of the interventional device. Upon rotation of the rotatable member relative to the base member, the longitudinal opening is selectively constrictable to comprise a seal around the interventional device.

In another version thereof, the present invention comprises a valve assembly. The valve assembly includes a cannula body, a base member, a rotatable member, and a valve sheath. The cannula body, base member, rotatable member and valve sheath each have a proximal end and a distal end. The cannula body proximal end is engaged with the base member distal end. The base member proximal end is engaged with the rotatable member distal end in a manner to permit rotation of the rotatable member relative to the base member. The cannula body, base member and rotatable member are aligned in the valve assembly to define an elongated passageway therethrough for passage of an interventional device. The valve sheath is disposed along the passageway and has a longitudinal opening therethrough for passage of the interventional device. The valve sheath distal end is secured to the base member and the valve sheath proximal end is secured to the rotatable member. The valve sheath is manipulatable when the rotatable member is rotated relative to the base member such that the longitudinal opening constricts to comprise a seal around the interventional device. The assembly may further include at least one valve disk disposed in the passageway between the cannula body and the base member. The valve disk has an axial opening therethrough which is conformable to the interventional device to comprise a seal when the device is disposed in the passageway.

In still another version thereof, the present invention comprises an iris valve assembly for controlling a flow of fluid. The assembly comprises a base member, a rotatable member engaged with the base member in a manner to permit rotation of the rotatable member relative to the base member, and an elastomeric valve member having a longitudinal opening therethrough and having respective longitudinal ends. One of the longitudinal ends is secured to the base member and the other longitudinal end is secured to the rotatable member. The base member, rotatable member and valve member are aligned such that an elongated passageway is defined through the assembly. The base member and rotatable member are provided with complementary ratcheting members, which ratcheting members are aligned in a manner to inhibit recoil of the rotatable member relative to the base member following rotation of the rotatable member.

BRIEF DESCRIPTION OF THE DRAWINGS

FIG. 9 is a perspective view of the valve sheath of FIG. 1;

FIG. 10 is a sectional view of the valve sheath taken along line 10—10 of FIG. 11;

FIG. 11 is an end view of the valve sheath, as viewed from the proximal end;

FIG. 19 is an alternative embodiment of the inventive valve assembly illustrating the presence of a locking device, showing the device in the unlocked position;

FIG. 20 shows the valve assembly of FIG. 19 in the locked position;

DETAILED DESCRIPTION

Figure 1:
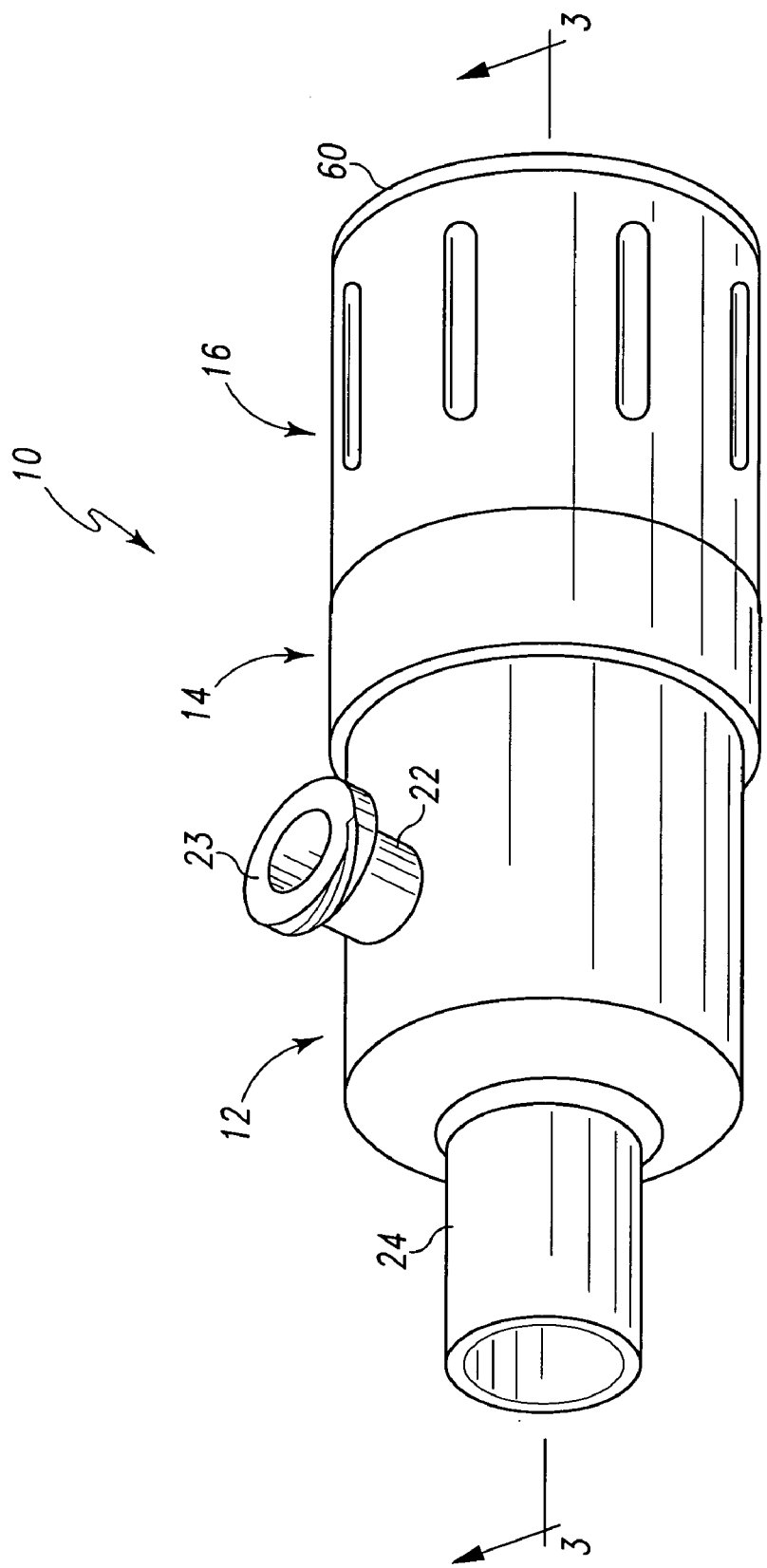
FIG. 1 is a perspective view of a hemostatic valve assembly according to an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the valve assembly, as well as the axial ends of various component features. The term "proximal" is used in its conventional sense to refer to the end of the assembly (or component thereof) that is closest to the operator during use of the assembly. The term "distal" is used in its conventional sense to refer to the end of the assembly (or component thereof) that is initially inserted into the patient, or that is closest to the patient.

Figure 2:
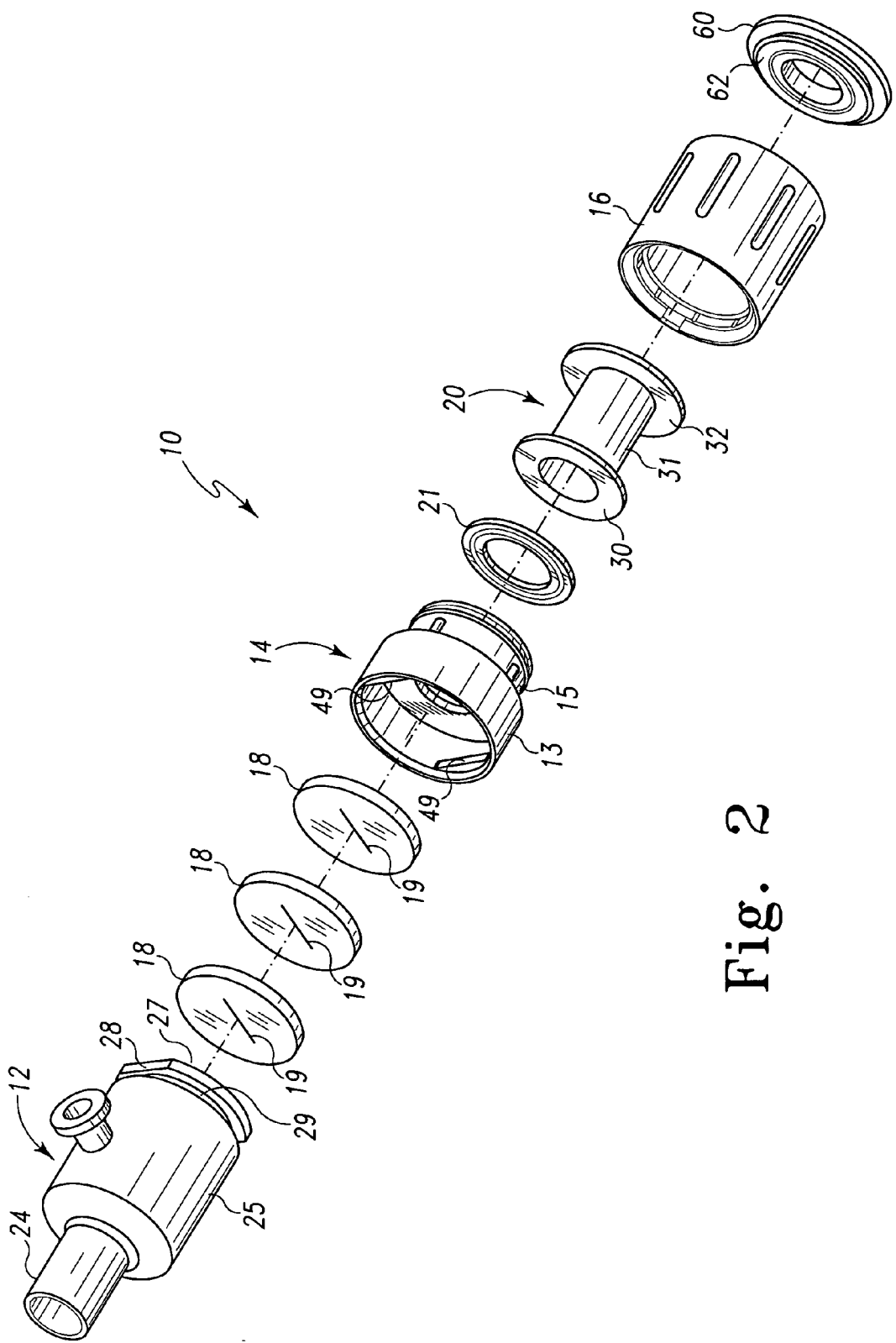
FIG. 2 is an exploded view of the hemostatic valve assembly of FIG. 1.
Figure 3:
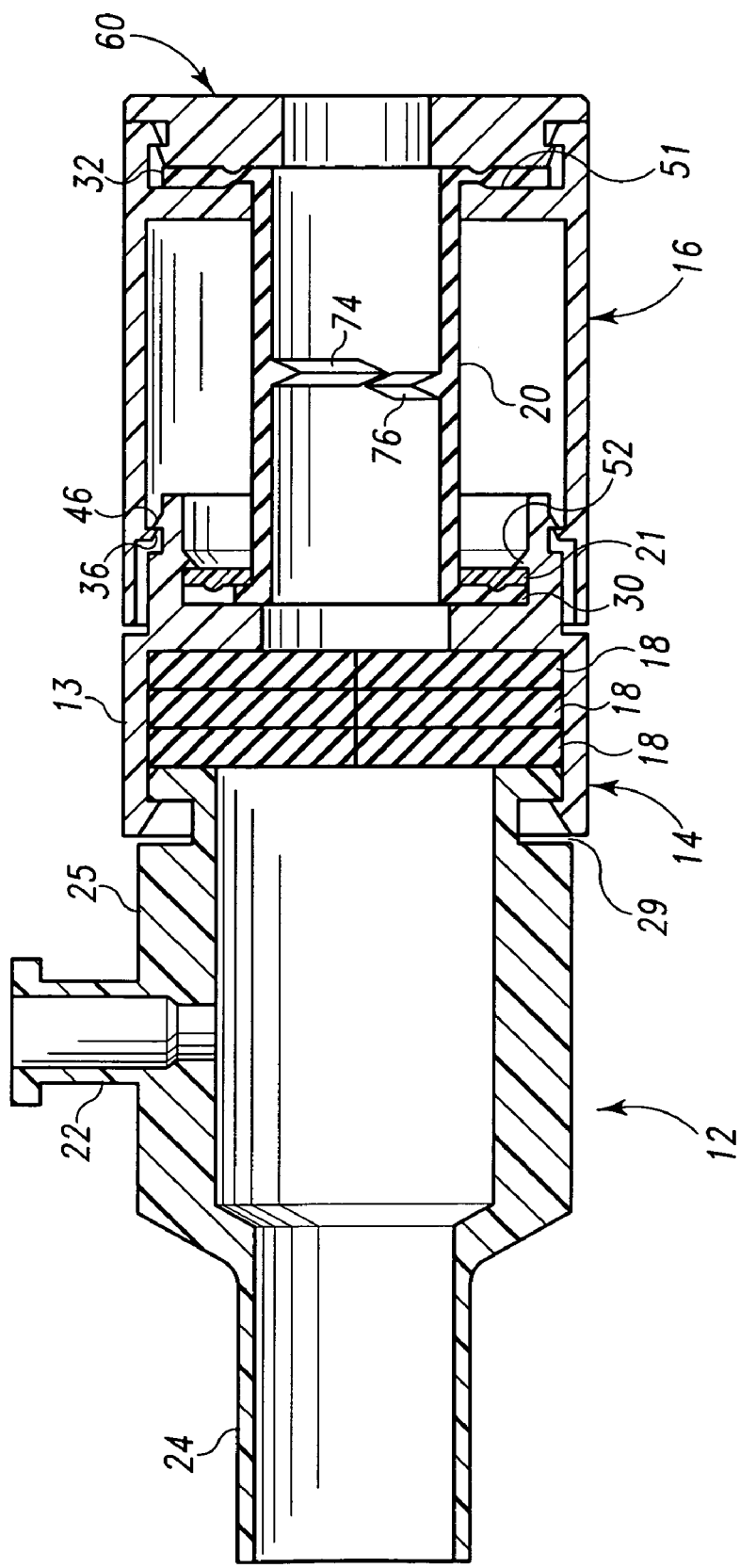
FIG. 3 is a longitudinal sectional view of the valve assembly of FIG. 1.

FIG. 1 illustrates a perspective view of a hemostatic valve assembly 10 according to an embodiment of the present invention. FIG. 2 illustrates an exploded view of hemostatic valve assembly 10 of FIG. 1, and FIG. 3 is a longitudinal sectional view of the hemostatic valve assembly of FIG. 1. Hemostatic valve assembly 10 includes a cannula body 12, a base member 14 and a rotatable member 16. A check valve is disposed longitudinally between cannula body 12 and base member 14. In the embodiment shown, the check valve comprises one or more (three are shown in the embodiment of FIG. 2) valve disks 18. An elastomeric valve sheath 20 of the "iris"-type is disposed between base member 14 and rotatable member 16. Iris valves are known in the art and are described, for example, in the incorporated-by-reference U.S. Pat. No. 5,158,553. A washer 21 is provided to secure a flanged end of the iris valve to the base member, in a manner to be described. An end cap 60 is provided at the proximal end of the device.

Figure 4:
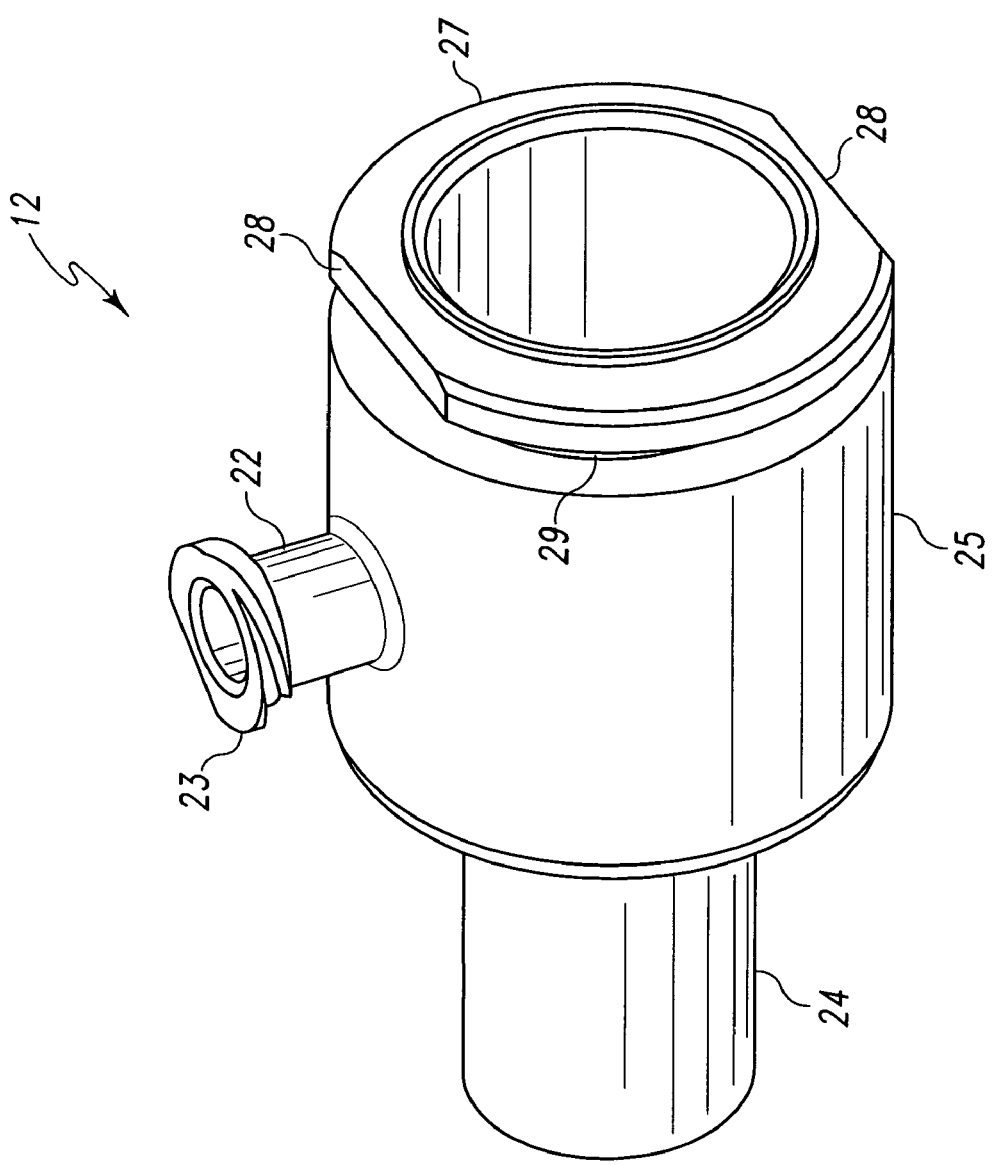
FIG. 4 is a perspective view of cannula body 12.

The components of valve assembly 10 will now be described in greater detail. Cannula body 12 is shown in FIG. 4. As illustrated, cannula body 12 comprises a generally cylindrical body 25 having a side-arm spout 22 extending transversely therefrom. Spout 22 includes a lip 23 sized and shaped for threaded or like engagement with a tube or other device (not shown) for transmittal or drainage of a fluid or a drug in conventional fashion. The distal end of cannula body 12 comprises a smaller diameter portion 24 for use in attaching valve assembly 10 to a medical device, such as an introducer sheath (not shown), in conventional fashion. In the preferred embodiment shown, an annular portion 27 is spaced from cylindrical body 25 at the proximal end of cannula body 12 for engagement with base member 14, in a manner to be described. Preferably, annular portion 27 includes two opposing flattened portions 28. Annular portion 27 is spaced from cylindrical body 25 by smaller diameter cylindrical portion 29.

Valve disks 18 are preferably conventional check flow disks. Such valve disks are commercially available, and may be obtained, for example, from Cook, Inc., of Bloomington, Ind., under the name CHECK-FLO® valves. Valve disks 18 include a slit 19 (FIG. 2) for passage of an interventional device (not shown) therethrough. Preferably, valve disks 18 have a slit on each face thereof, only one of which is visible in the orientation of FIG. 2. The slits may extend either partially or fully through the disk. Disks of this type are well known in the art. Preferably, three valve disks are stacked and arranged such that the slits are aligned as shown in FIG. 2. However, those skilled in the art will appreciate that other numbers of disks may be utilized, and the alignment of the slits in the disks need not be as shown in the figures.

Figure 5:
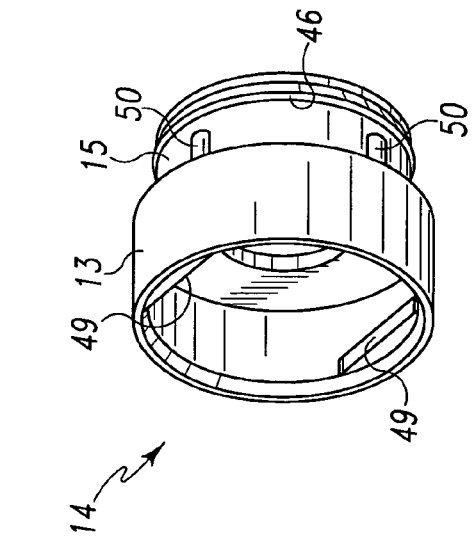
FIG. 5 is a perspective view of the base member of the embodiment of FIG. 1 illustrating features of the proximal end of the base member.
Figure 6:
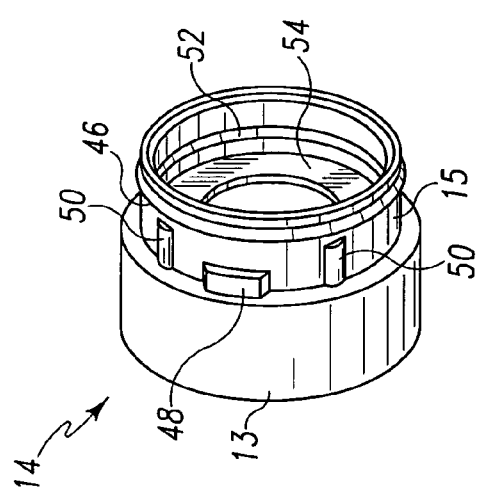
FIG. 6 is a perspective view of the base member of the embodiment of FIG. 1 illustrating features of the distal end of the base member.

FIGS. 5 and 6 illustrate the features of base member 14 in greater detail. FIG. 5 illustrates the features of the base member when viewed from a proximal perspective, and FIG. 6 illustrates the features of the base member when viewed from a distal perspective. Base member 14 includes a large diameter cylindrical portion 13 and a small diameter cylindrical portion 15. As illustrated in FIG. 5, base member 14 comprises external snap ring 46, positive stop member 48 and internal snap ring 52. A plurality of ratcheting rib members 50 (two of which are visible in FIG. 5) are spaced along the outer circumference of base member small diameter portion 15.

As illustrated in FIG. 6, base member 14 also includes opposing flattened portions 49. Flattened portions 49 project radially into the inner circumference of base member 14. Flattened portions 49 are sized and spaced such that when cannula body 12 and base member 14 are engaged as shown in FIG. 1, flattened portions 49 adjoin and rest upon corresponding cannula body flattened portions 28. In this manner, the cannula body and base member are essentially locked together, thereby preventing relative rotation therebetween.

Figure 7:
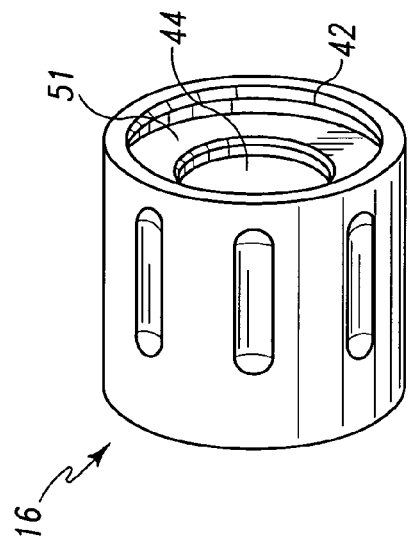
FIG. 7 is a perspective view of the rotatable member of the embodiment of FIG. 1 illustrating features of the distal end of the rotatable member.
Figure 8:
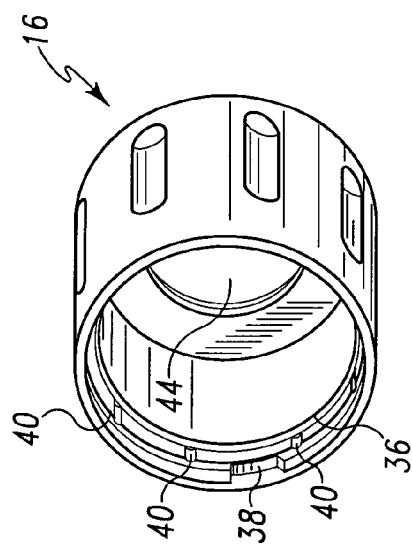
FIG. 8 is a perspective view of the rotatable member of the embodiment of FIG. 1 illustrating features of the proximal end of the base member.

FIGS. 7 and 8 illustrate the features of rotatable member 16 in greater detail. FIG. 7 illustrates the features of the rotatable member when viewed from a distal perspective, and FIG. 8 illustrates the features of the rotatable member when viewed from a proximal perspective. As illustrated in FIG. 7, rotatable member 16 comprises snap ring 36 and positive stop member 38. A plurality of ratcheting rib members 40 are spaced along the inner circumference of rotatable member 16. Rotatable member snap ring 36 is utilized for engaging external snap ring 46 of base member 14. Positive stop member 38 and ratcheting rib members 40 are used as described below. As illustrated in FIG. 8, rotatable member 16 also includes snap ring 42 at its proximal end for engagement with a reciprocal snap ring on end cap 60.

FIGS. 9–11 illustrate the features of one embodiment of an elastomeric valve sheath in greater detail. In the embodiment shown, elastomeric valve sheath 20 comprises a generally cylindrical body 31 having annular flange 30 at its distal end and annular flange 32 at its proximal end. Preferably, as shown in FIGS. 10 and 11, valve sheath 20 includes a ribbed structure that projects radially into the center of the valve sheath from the inner surface of the valve sheath. The projecting ribbed structure is believed to enhance the seal formed by the valve sheath by inhibiting the possibility of gap formation when the iris valve is closed. The formation of longitudinal gaps can be problematic with conventional iris seals, particularly when smaller diameter interventional devices are inserted therethrough. An optional slot 33 is provided at annular flange 30, however a similar slot may also be provided at annular flange 32 if desired. Slot 33 simply provides a space that can be filled by portions of the elastomeric valve sheath when the sheath is compressed.

As shown in FIGS. 10 and 11, the ribbed structure comprises one or more segments that extend circumferentially along part, or all, of the internal circumference of the valve member. Preferably, the ribbed structure is positioned substantially at or near the axial midpoint of the valve sheath. In the embodiment shown, the ribbed structure comprises rib members 74, 76, 78. Rib members 74, 76, 78 are circumferentially spaced along inner valve surface 72, and are slightly axially offset from each other. Each of rib members 74, 76, 78 spans about one-third of the inner circumference of the valve member, such that in combination as shown, the rib members substantially span the entire inner circumference of the valve member. The longitudinal ends of each of the rib members preferably overlap slightly as the members are spaced along the circumference of the inner surface of the valve sheath, as shown in FIG. 11. Preferably, the ribbed members have a generally triangular shape in cross-section as shown in FIG. 10, although other shapes may be substituted. It is believed that when the iris valve is closed, the presence of the rib members 74, 76, 78 interact to comprise a lock (similar to that provided in well-known plastic locked bags) that is capable of providing a substantially gap-free seal. The sealing capability of the rib members is believed to be further enhanced when they are slightly axially offset as shown. In this arrangement, the rib members may meet in the center of the valve upon closure to provide additional sealing capability.

Although the annular structure that extends along the interior surface of valve sheath 20 has been described as a ribbed structure, other configurations may be substituted.

For example, the structure can simply comprise an annular ring that extends circumferentially along the inner surface of valve sheath 20, preferably at or about the longitudinal center of the valve sheath. In addition, the ribbed or similar structure can also have other sizes, shapes and configurations. For example, the rib can be annular and extend around the inner surface of the valve, or any segment of the inner surface. Alternatively, the rib can be spiral and extend in helical fashion along the inner surface as a complete spiral, or as one or more spiral rib segments. As another alternative, the ribbed structure can comprise any number of discrete rib members that span in any fashion the whole, or any desired partial portion of, the inner circumference of the valve member. Furthermore, the discrete rib members can be axially arranged along the same horizontal plane of the circumferential surface, or alternatively, can be axially offset in any desired configuration along that inner circumference. In still further possible configurations, the rib member(s) of any of the preceding configurations can be aligned to extend parallel to the axis of the valve member, rather than transversely as shown in the figures, or the assembly can include a combination of parallel and transverse rib members.

Figure 17:
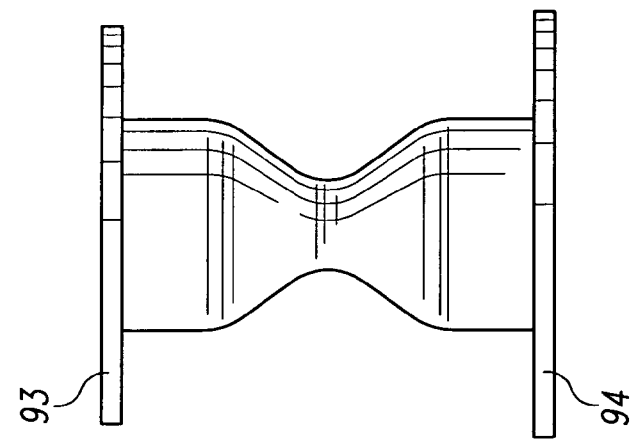
FIGS. 16 and 17 are alternative embodiments of a valve sheath.
Figure 16:
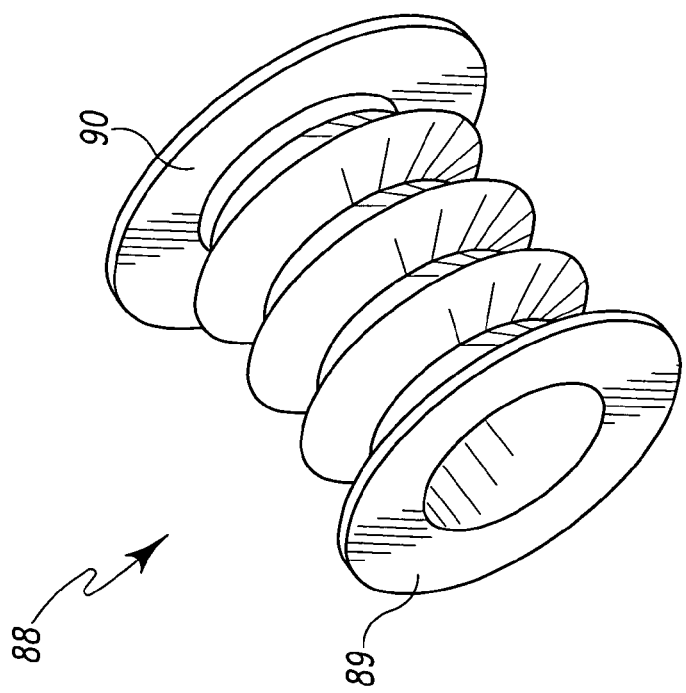

In addition to the valve sheath 20 having the cylindrical cross-section as shown, the valve sheath can have other cross-sectional configurations. Non-limiting examples of such configurations include a valve having an accordion-like shape or a valve having an hour-glass shape. An accordion-type valve 88 is shown in FIG. 16, and an hour-glass valve 92 is shown in FIG. 17. Accordion-type valve 88 includes end flanges 89, 90, and hour-glass valve 92 includes end flanges 93, 94, as before. Still other geometrical-shaped cross-sections may be utilized if desired. Non-limiting examples of such shapes include rectangular, triangular or diamond shapes. If desired, these alternative configurations can also be provided with the annular or ribbed sealing structure as described.

Figure 13:
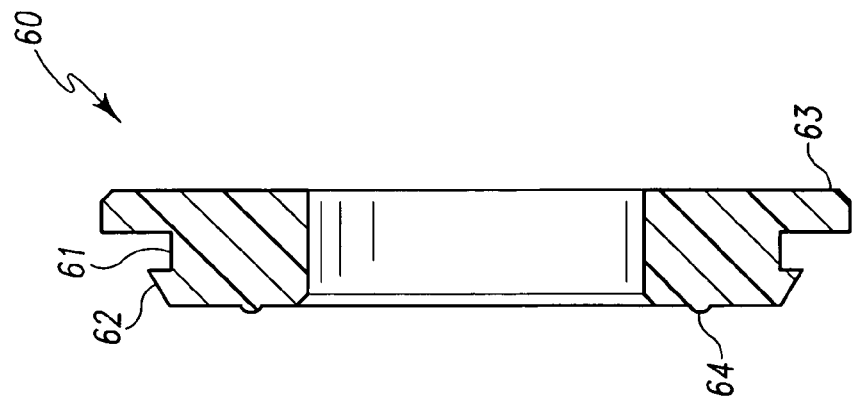
FIG. 13 is a sectional view of the end cap of FIG. 12.
Figure 12:
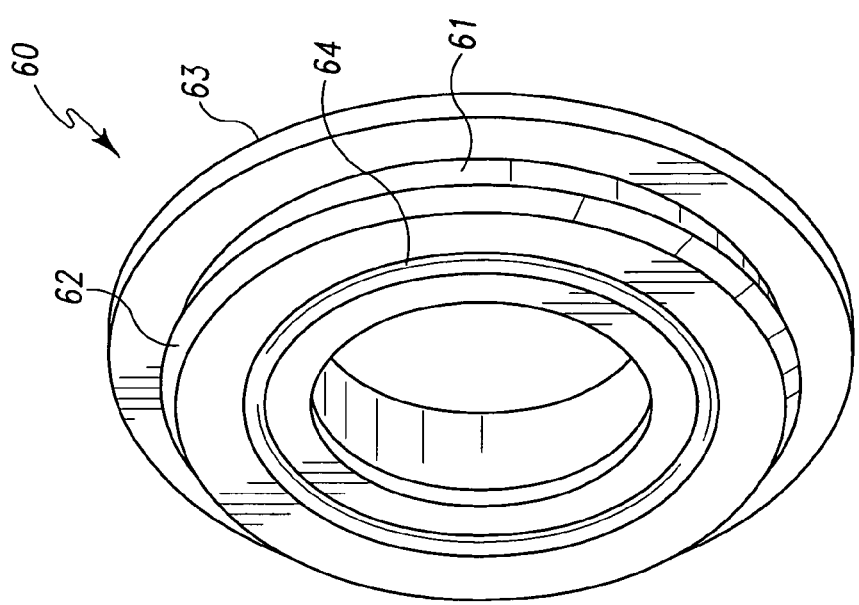
FIG. 12 is a perspective view of the end cap of the embodiment of FIG. 1.

FIGS. 12 and 13 illustrate the features of the end cap 60. End cap 60 includes a snap ring 62 that is spaced from main body 63 of end cap 60 by a small diameter portion 61. Snap ring 62 is sized for engagement with corresponding snap ring 42 on rotatable member 16 to enable a snap fit therebetween. A pressure ring 64 may be provided for enhancing the seal between end cap 60 and rotatable member 16 in conventional fashion.

Cannula body 12, base member 14, rotatable member 16, washer 21 and end cap 60 are preferably formed of a machined or injection molded relatively hard polymeric material, such as acetal, polypropylene, ABS, nylon, PVC, polyethylene or polycarbonate. As illustrated, each of the aforementioned constituents includes a hollowed-out center portion to enable passage of an interventional device therethrough.

Valve sheath 20 is preferably elastomeric, and more preferably, is formed of injection molded silicone. A non-limiting list of other suitable materials for use in forming the valve member includes isoprene, latex and various rubber or polymeric compositions. For the purposes of the present invention, the durometer of the valve member should be considerably less than the durometer of the body, base and rotatable members, resulting in a valve sheath that is softer and more flexible than the remaining structure. If desired, the valve sheath, or preferably, the internal surface only of the valve sheath, can be coated with a lubricious coating, such as parylene, to improve the lubricity of the surface and facilitate the passage of the device therethrough.

Hemostatic valve assembly 10 may be assembled in the following manner. Initially, valve disks 18 are aligned as described above, and loaded into base member large diameter portion 13. Base member large diameter portion 13 is then engaged with cannula body 12 by a snap fit. Respective cannula body flattened portions 28 and base member flattened portions 49 are aligned such that the flattened portions engage each other, thereby preventing relative rotation between cannula body 12 and base member 14. Valve disks 18 are compressed into the space between cannula body 12 and base member 14, as shown in FIG. 3.

Those skilled in the art will appreciate that base member 14 and cannula body 12 need not be attached by the method described, and other well-known methods of affixation of two parts may be substituted. However, best results are obtained when relative rotation between the two parts is prevented. The insertion and capture of valve disks between two substrates is well-known in the medical arts, and those skilled in the art will appreciate that other suitable ways of capturing these valve disks may be substituted for those described.

Washer 21 is fitted over the generally cylindrical body 31 of elastomeric valve sheath 20 by any convenient method, such as by temporarily compressing one of the axial annular flanges 30, 32 and simply sliding washer 21 over the compressed flange and onto cylindrical body 31. Distal flange 30 of valve sheath 20 is axially aligned with valve-receiving surface 54 (FIG. 5) of base member 14. Washer 21 is then urged in the distal direction against distal flange 30 toward snap ring 52. The washer is sized relative to the snap ring and the inner surface of base member small diameter portion 15 such that it "snaps" into place between snap ring 52 and valve-receiving surface 54 when it is urged in the distal direction, thereby creating a snap fit of washer 26 and distal flange 30 against valve-receiving surface 54 (FIG. 3). Snap ring 52 is spaced from surface 54 a defined distance, such that upon the snap fit of the washer and flange as described, washer 21 compresses flange 30 against surface 54. Flange 30 is thereby secured in base member 14, such that it is prevented from rotating, disengaging or otherwise separating from base member 14 during use of the valve assembly.

Figure 18:
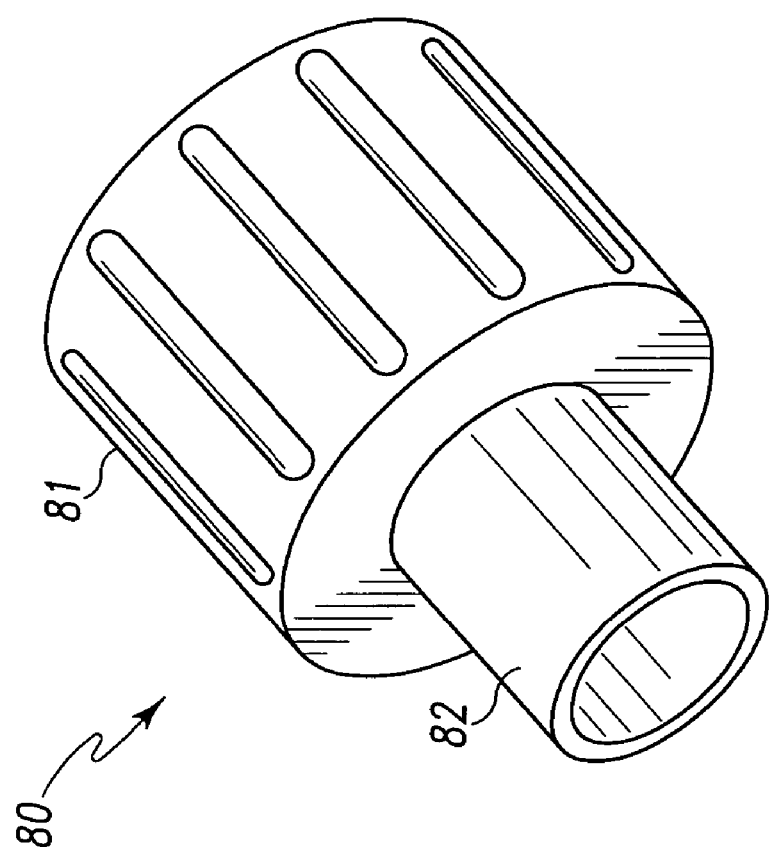
FIG. 18 is a perspective view of a pusher assembly that may be used to assemble portions of the inventive valve assembly.
Figure 23:
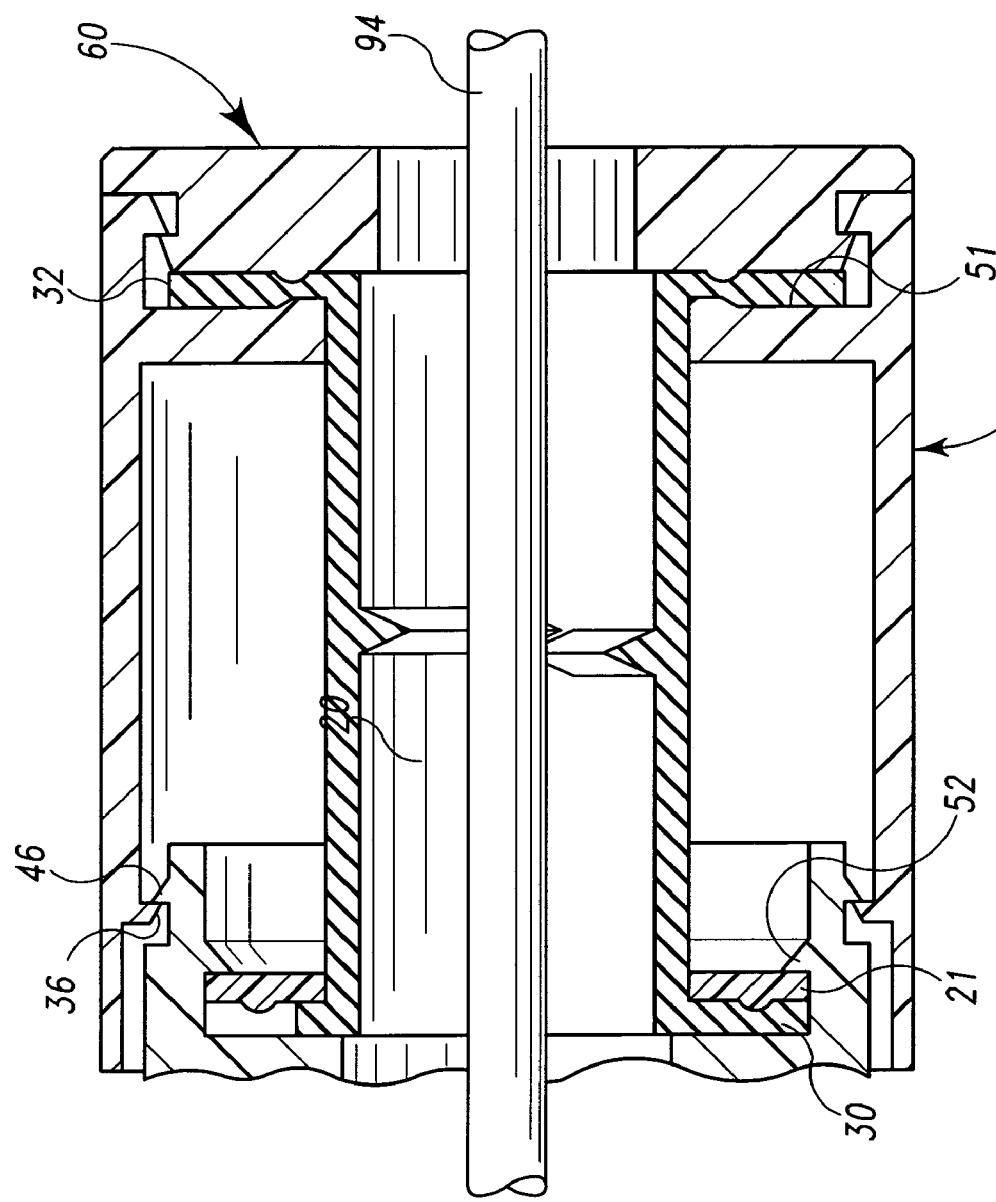
FIG. 23 is a sectional view of a portion of the assembly of FIG. 3, showing the presence of an interventional device extending through the assembly.

If desired, an assembly tool may be utilized to facilitate the snap fit. An example of one such assembly tool 80 is illustrated in FIG. 18. Assembly tool 80 may be formed of a machined or injection molded relatively hard polymeric material, such as the materials previously described for use in forming the cannula body, base member, rotatable member and snap cap. As shown in FIG. 23, assembly tool 80 includes a generally cylindrical main body portion 81, and a small diameter portion 82. Small diameter portion 82 has an outer diameter substantially the same as the outer diameter of washer 21. Tool 80 can be utilized to urge washer 21 in the distal direction until it passes snap ring 52, and is thereby snapped into place. As a result, elastomeric valve flange 30 is compressed by washer 21 against the valve-receiving surface of base member 14. Those skilled in the art will appreciate that numerous other convenient ways of urging washer 21 past snap ring 52 in the distal direction may be substituted.

Base member 14 and rotatable member 16 are engaged by loosely snapping together base member snap ring 46 and rotatable member snap ring 36 to establish a loose snap fit therebetween. The engagement of base member 14 and rotatable member 16 must be loose enough to allow relative rotation therebetween, but secure enough to prevent disengagement during use. This engagement is best shown in FIG. 3. Those skilled in the art will recognize that other attachment mechanisms may be substituted for the mechanism described, as long as relative rotation is maintained between the base member and the rotatable member, and the members are aligned such that they do not disengage during normal use of the device.

Proximal flange 32 of the elastomeric valve member is extracted through rotatable member through-hole 44 (FIG. 8) in the proximal direction by any convenient means, such as by pulling flange 32 through the hole with tweezers. With proximal flange 32 resting on rotatable member valve-receiving surface 51, end cap 60 is engaged with rotatable member 14 by, e.g., creating a snap fit between respective rotatable member snap ring 42 and end cap snap ring 62. The snap fits described hereinabove can be accomplished in any convenient fashion, such as by use of a small hand press, or by simply snapping end cap 60 into place at the proximal end of rotatable member 16 in any convenient manner. Alternatively, instead of a snap fit, those skilled in the art will appreciate that other engagement means known in the art can be substituted, such as mating screw threads or a friction fit. When the device is assembled, elastomeric valve flange 32 is compressed against valve-receiving surface 51 of rotatable member 16, in a similar manner as the previously-described compression of elastomeric valve flange 30 against the valve-receiving surface 54 of base member 14.

When rotatable member 16 of valve assembly 10 is rotated relative to base member 14 during use of the inventive hemostatic valve assembly, respective positive stop members 38, 48 are sized and shaped to abut each other to limit the degree of rotation. Preferably, rotation is limited to 345° or less. In the embodiment shown, positive stop member 38 on the rotatable member is recessed to allow for clearance of ratcheting rib members 50 on base member 14, as described below.

In the preferred embodiment of FIGS. 5–8, base member 14 includes four ratcheting rib members 50 angularly spaced along the outer circumference of base member small diameter portion 15, and rotatable member 16 includes eight ratcheting rib members 40 spaced along the inner circumference of rotatable member 16. When base member 14 and rotatable member 16 are snap fit together as described, rib members 50 of the base member and complementary rib members 40 of the rotatable member are circumferentially aligned to provide a ratcheting action upon rotation of rotatable member 16. Ratcheting of these members in this fashion inhibits recoil of the rotatable member 16, end cap 60 and valve sheath 20 with respect to base member 14 during rotation.

The number of ratcheting rib members on each of members 14 and 16 is exemplary only, and other numbers of such ratcheting members may be substituted, as long as the objective of inhibiting recoil of rotatable member 16 may be met. In addition, the ratcheting members need not all be rib-like as described. For example, a combination of ribs and grooves may also be utilized to inhibit recoil. One preferred embodiment includes providing rib members on base member 14 and corresponding grooves on rotatable member 16. This arrangement can be reversed if desired. That is, rib members may be provided on the rotatable member and the corresponding grooves may be provided on the base member. The ratcheting members can be positioned in complementary arrangements other than those specifically described to enable valve sheath 20 to provide a seal around devices of varying diameters. If desired, the spacing of the ratcheting members can be optimized depending upon the diameter of the device passing through. The ratcheting members need not be evenly spaced, and they can be offset or otherwise varied depending upon the configuration and type of device passed therethrough, as long as the ratcheting feature may be obtained. Ratcheting of one device relative to another is well-known in the art, and other mechanisms for achieving this action may likewise be substituted.

Recoil also may be inhibited by other well-known mechanisms suitable for this purpose. For example, rather than utilizing ratcheting rib members, or rib and groove members on the designated surfaces of the base and rotatable members, one or both of engaging surfaces can be knurled or otherwise provided with a roughened texture. In such instance, recoil would be inhibited by friction generated by the relative movement of such knurled or roughened surface (s).

Figure 15:
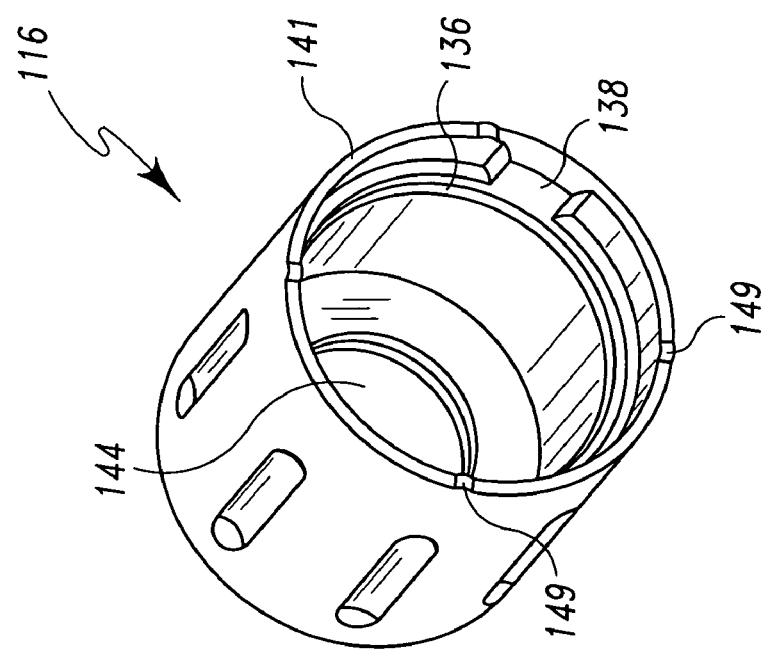
FIG. 15 is a perspective view of an alternative embodiment of a rotatable member, for use with the base member of FIG. 14.
Figure 14:
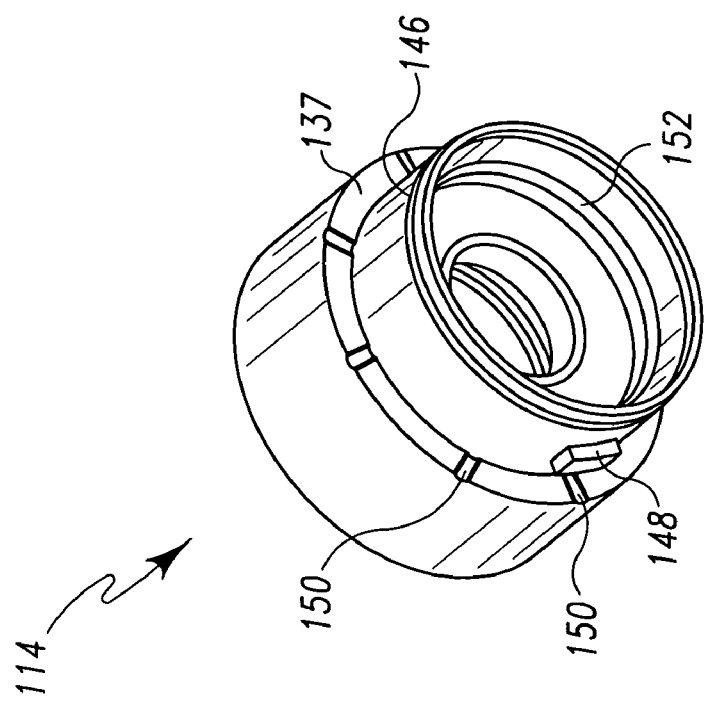
FIG. 14 is a perspective view of an alternative embodiment of a base member.

An alternative means for inhibiting recoil is shown in FIGS. 14 and 15. In this embodiment, base member 114 is provided with snap ring 146, positive stop member 148 and snap ring 152. A ledge 137 is provided, having a plurality of grooves 150 distributed therealong. Grooves 150 can be randomly placed, or can be positioned at fixed locations along ledge 137. In the embodiment shown, there are eight grooves spaced approximately forty-five degrees apart. Rotatable member 116 comprises snap ring 136, positive stop member 138, and through-hole 144 as before. Rotatable member 116 is provided with ridges 149 that project (axially) outwardly from an edge 141 of rotatable member 116. Ridges 149 can be randomly spaced, or can be placed at fixed locations along edge 141. In the embodiment shown, four ridges 149 are spaced ninety degrees apart. In this embodiment, the ratcheting action is achieved during rotation of rotatable member 116 relative to base member 114 as a result of the interaction between ridges 149 and grooves 150, as the ridges pass into, and out of, the grooves during such rotation.

The arrangement of FIGS. 14 and 15 may likewise be varied by placing the grooves on the rotatable member and the corresponding ridges on the base member. Any number of grooves and ridges may be utilized for a particular purpose. Those skilled in the art will recognize that grooves and ridges must be sized and shaped to complement one another such that the ratcheting action may be achieved. In other words, the grooves and ridges must be sized such they are capable of interconnecting following rotation of rotatable member 116, to inhibit unintended recoil of member 116 relative to member 114.

Figure 24:
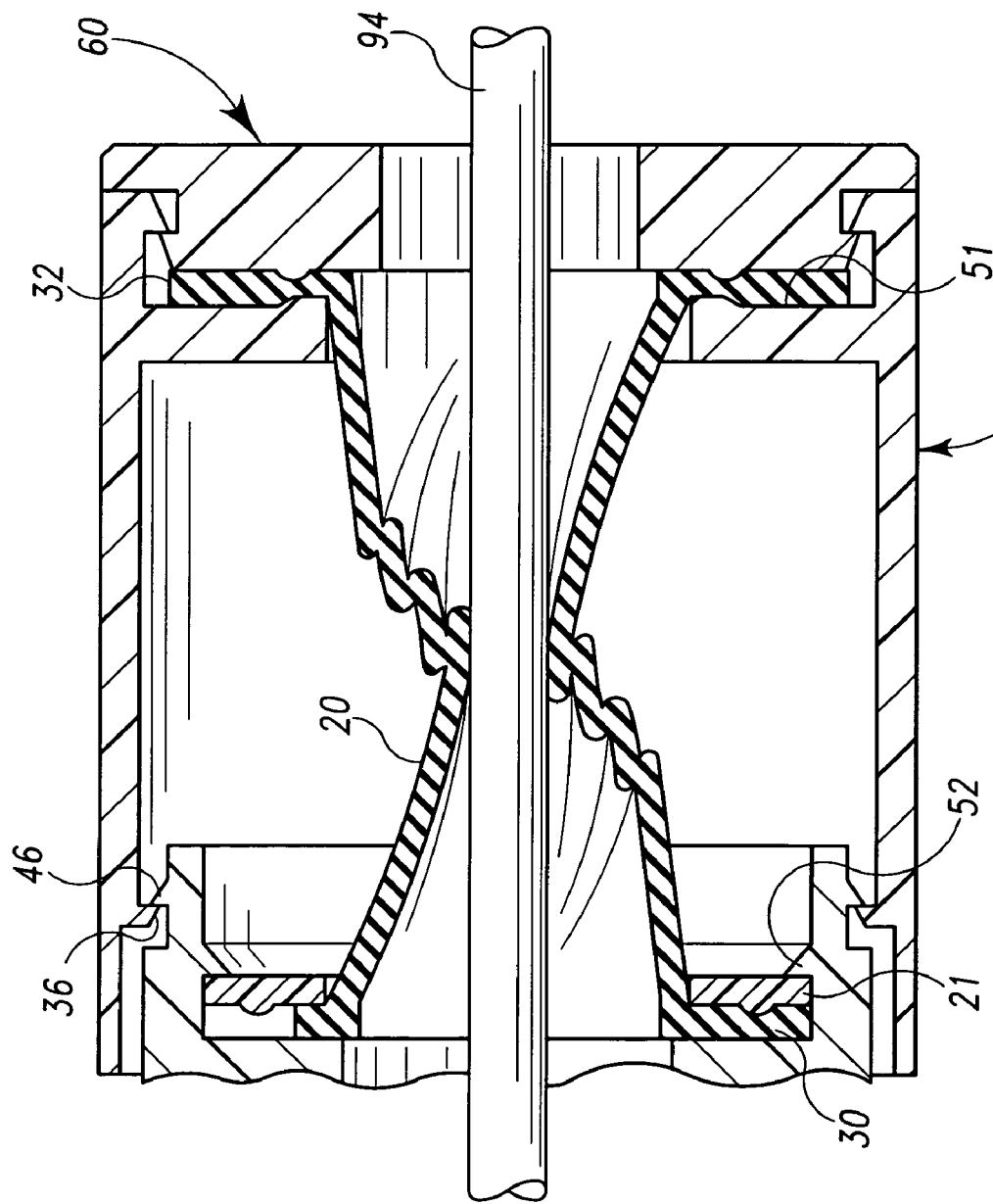
FIG. 24 is a sectional view the portion of the assembly with an interventional device shown in FIG. 23, with the elastomeric valve in the closed position.

Operation of the iris valve portion of the hemostatic valve assembly 10 is illustrated in FIGS. 23 and 24. Operation is commenced when the operator grasps rotating rotatable member 16, and rotates this member relative to base member 14. Since distal flange 30 and proximal flange 32 of valve sheath 20 are fixedly secured in the respective distal and proximal ends of the valve assembly as described, rotation of member 16 causes an axially intermediate portion (existing between the fixed distal and proximal flanges 30, 32) of the soft polymeric material of the valve member 20 to twist on itself from the opened position of FIG. 23, to a closed position shown in FIG. 24. As shown in FIG. 24, the center opening of the valve is twisted, and thereby constricts around an interventional device, in this case dilator 94. Constriction of a center passageway of an iris valve in this manner is known in the art, and is further described and illustrated in the incorporated-by-reference U.S. Pat. No. 5,158,553. Such constriction results in the formation of a hemostatic seal between the valve and an interventional device inserted therethrough.

One problem that has existed in the art with reference to such valves has been the manner of engaging the proximal and distal ends of the valve in the respective base and rotatable members. In the preferred embodiment of the present invention, valve member 20 is provided with distal and proximal flanges 30, 32, which are capable of being snapped or otherwise securely affixed into position in the respective base and rotatable members, as described. The snap fit is tight enough to compress the respective flanges against the receiving surface of the base member or rotatable member to prevent rotation of the respective flanges, and to ensure that the axial ends of the valve do not become disengaged from the assembly under conditions of normal use.

Although it is believed that the above-described valve assembly may be utilized with sheaths of virtually all sizes, it is believed that it will be particularly effective for use with larger valve sheaths. Large valve sheaths, such as those between about 12 French and 36 French and even larger, are often difficult to seal, and have been prone to the formation of axial gaps in the seals. The iris-type closure utilized in the inventive device provides a particularly effective seal for an introducer sheath or like medical device when catheters or other introducer devices of varying diameters are introduced therein, and also when no catheter is introduced and the lumen of the introducer must be maintained in a closed, leakproof condition. The seal also has a high resistance to tearing when penetrated by large diameter catheters, and is capable of tolerating repeated catheter insertions and withdrawals without any appreciable decrease in performance characteristics of the seal or valve.

Although the hemostatic valve assembly 10 of the present invention preferably includes one or more valve disks 18 in combination with valve sheath 20, the presence of a secondary valve source, such as the valve disks, is not necessarily required. In this event, the cannula body 12 may be omitted, and its features may be combined in a discrete base member 14. Base member 14 may be shaped or otherwise configured for attachment to an introducer sheath, and/or may include a side arm spout for transmittal or drainage of a fluid or a drug as described.

Another variation of the invention is shown in FIGS. 19 and 20. In this embodiment, valve assembly 200 includes cannula body 212, base member 214, rotatable member 216, end cap 260 and an elastomeric valve member (not shown), as described in previous embodiments. An annular groove 208 is provided at the proximal end of the valve assembly. Groove 208 may be provided along an inner circumference of the end cap, or alternatively, along an inner surface of the rotatable member. As shown in FIG. 19, a dilator 205 is passed through the inner passageway of the valve assembly. Dilator 205 is provided with a locking rib 209 that is sized and shaped to snap into groove 208 when dilator 205 is axially moved in the distal direction. A larger diameter washer 206 or similar mechanism is fashioned to allow selective engagement or disengagement of the locking rib.

Figure 21:
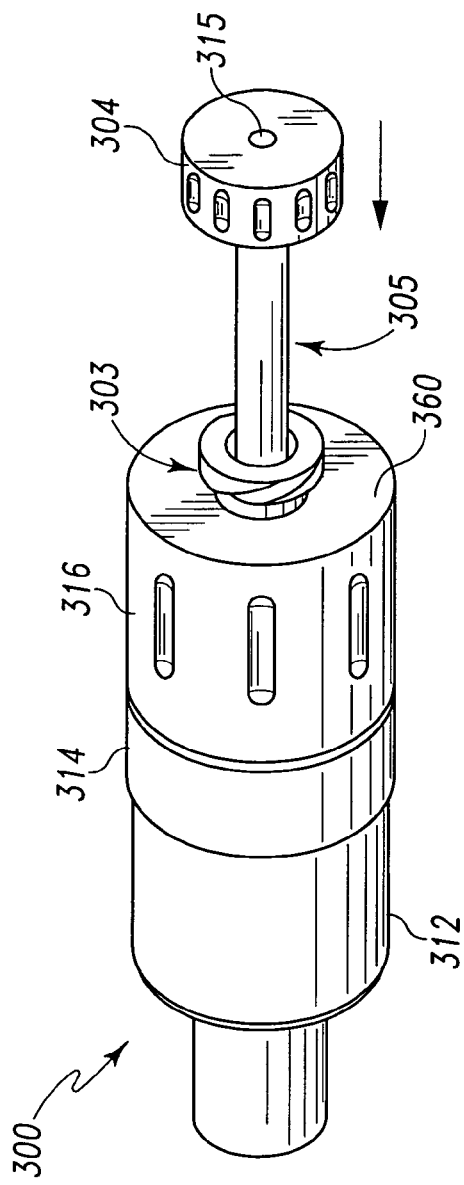
FIG. 21 is another alternative embodiment of the inventive valve assembly illustrating another type of locking device, showing the device in the unlocked position.
Figure 22:
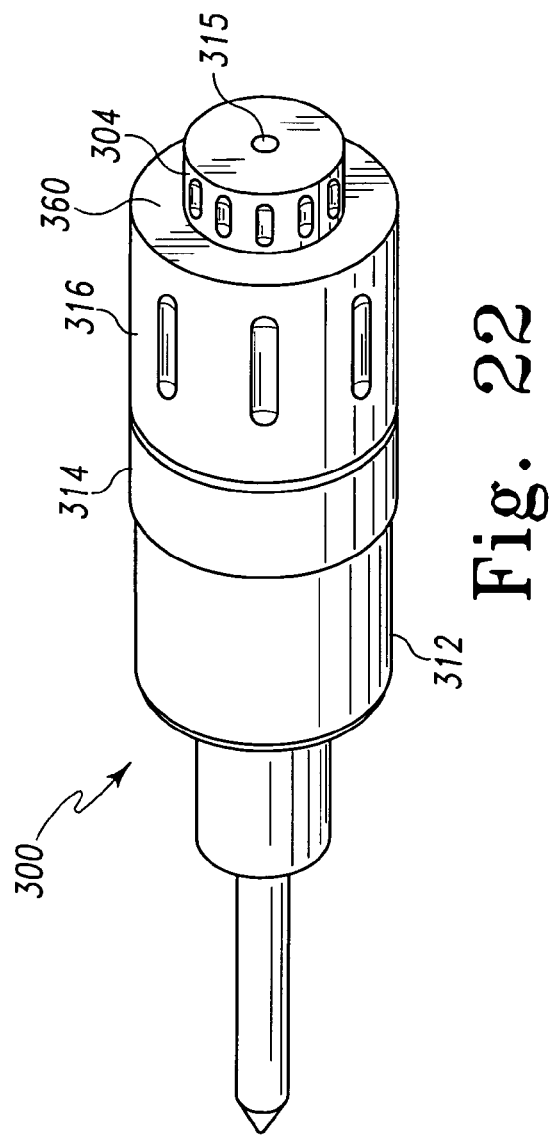
FIG. 22 shows the valve assembly of FIG. 21 in the locked position.

A variation of the embodiment of FIGS. 19–20 is shown in FIGS. 21 and 22. In this embodiment, valve assembly 300 includes cannula body 312, base member 314, rotatable member 316, end cap 360 and an elastomeric valve member (not shown), as before. The proximal end of valve assembly 300 includes a threaded collar 303. Dilator 305 is provided with a threaded cap having internal screw threads (not shown) that are threadedly received by threaded collar 303 is conventional fashion. Wire guide passageway 315 may extend longitudinally through assembly 300.

Those skilled in the art will recognize that other known locking assemblies can be substituted for the groove and rib connection, and the threaded connection shown in the embodiments of FIGS. 19 to 22. The embodiments shown are intended to illustrate only some of the possible mechanisms by which the dilator may be locked to the valve assembly.

While this invention has been particularly shown and described with reference to preferred embodiments thereof, it will be understood by those skilled in the art that various changes in form and details may be made therein without departing from the spirit and scope of the invention. Those skilled in the art may recognize or be able to ascertain using no more than routine experimentation, many equivalents to the specific embodiments of the invention described specifically herein, which equivalents are intended to be encompassed in the scope of the invention.

The invention claimed is:

1. A valve assembly for controlling a flow of fluid therethrough, comprising:
   a cannula body;
   a base member;
   a rotatable member;
   a valve sheath; each of said cannula body, base member, rotatable member and valve sheath having a proximal end and a distal end, said cannula body proximal end engaged with said base member distal end, said base member proximal end engaged with said rotatable member distal end in a manner to permit rotation of said rotatable member relative to said base member; said cannula body, base member and rotatable member aligned in said valve assembly to define an elongated passageway therethrough for passage of an interventional device, said valve sheath disposed along said passageway and having a longitudinal opening therethrough for passage of said interventional device, said valve sheath distal end being secured to said base member and said valve sheath proximal end being secured to said rotatable member, at least one of said valve sheath ends comprising a flange, at least one of said base member and rotatable member comprising a valve-receiving surface for receiving said flange; and
   a compression member for compressing said flange against said valve-receiving surface; a portion of said valve sheath being manipulatable when said rotatable member is rotated relative to said base member such that said valve sheath portion is twisted in a manner to constrict said longitudinal opening to comprise a seal around said interventional device when said interventional device is disposed in said passageway;
   said valve assembly further comprising at least one valve disk disposed in said passageway between said cannula body and said base member, said valve disk having opposing axial ends, and having a generally axial opening between said opposing axial ends for passage of said interventional device, said axial opening conformable to said interventional device to comprise a seal when said device is disposed in said passageway.

2. The valve assembly of claim 1, wherein said at least one valve disk comprises a slit at each axial end, each said slit extending axially into said disk toward said opposing axial end without passing entirely through said disk.

3. The valve assembly of claim 1, wherein said at least one valve disk comprises at least three valve disks, each said disk including a slit at each axial end thereof, said slits axially extending at least partially through said disk.

4. The valve assembly of claim 1, wherein each of said base member and rotatable member comprise a valve-receiving surface and wherein each of said valve sheath ends comprises a flange, each of said flanges being secured at a separate one of said base member and said rotatable member by compression of said flange against said valve-receiving surface.

5. The valve assembly of claim 1, wherein each of said base member and said rotatable member comprise one or more ratcheting members, said base member ratcheting members engageable with said rotatable member ratcheting members to inhibit recoil of said rotatable member following rotation of said rotatable member relative to said base member.

6. The valve assembly of claim 1, wherein each of said base member and said rotatable member comprise a stop member, each of said stop members being complementary to the other stop member for limiting rotation of said rotatable member relative to said base member.

7. The valve assembly of claim 1, wherein said valve sheath comprises a generally cylindrical configuration, an accordion-like configuration or an hour-glass configuration.

8. The valve assembly of claim 1, wherein at least the inner surface of the valve sheath includes a lubricous coating.

9. The valve assembly of claim 1, wherein said valve sheath further comprises a ribbed element projecting radially into the center of the sheath.

10. The valve assembly of claim 1, wherein said base member comprises said valve-receiving surface and said valve sheath distal end comprises said flange, said compression member comprising a washer for compressing said flange against said valve-receiving surface.

11. The valve assembly of claim 1, wherein said rotatable member comprises said valve-receiving surface and said valve sheath proximal end comprises said flange, said compression member comprising an end cap for compressing said flange between said rotatable member and said end cap.

12. The valve assembly of claim 1, wherein said cannula body and base member are provided with respective flattened portions, said cannula body flattened portions in abutment with said base member flattened portions to prevent relative rotation between said cannula body and said base member.

13. The valve assembly of claim 9, wherein said ribbed element comprises at least three rib segments.

14. The valve assembly of claim 9, wherein said ribbed element extends substantially around the inner circumference of the sheath.

* * * * *